United States Patent
Altshuler et al.

(10) Patent No.: US 11,307,365 B2
(45) Date of Patent: Apr. 19, 2022

(54) OPTICAL FIBER CABLE CONNECTOR

(71) Applicant: IPG Photonics Corporation, Oxford, MA (US)

(72) Inventors: Gregory Altshuler, Lincoln, MA (US); Christopher Gaal, Mansfield, MA (US); Valery Kozlov, Lexington, MA (US)

(73) Assignee: IPG Photonics Corporation, Oxford, MA (US)

( * ) Notice: Subject to any disclaimer, the term of this patent is extended or adjusted under 35 U.S.C. 154(b) by 0 days.

(21) Appl. No.: 16/883,601

(22) Filed: May 26, 2020

(65) Prior Publication Data

US 2021/0048586 A1    Feb. 18, 2021

Related U.S. Application Data

(63) Continuation of application No. 16/141,381, filed on Sep. 25, 2018, now Pat. No. 10,663,677, which is a
(Continued)

(51) Int. Cl.
*G02B 6/38* (2006.01)
*G02B 6/42* (2006.01)
(Continued)

(52) U.S. Cl.
CPC ............. *G02B 6/3882* (2013.01); *A61N 5/06* (2013.01); *G02B 6/3624* (2013.01);
(Continued)

(58) Field of Classification Search
CPC .............................. G02B 6/3865; G02B 6/4253
See application file for complete search history.

(56) References Cited

U.S. PATENT DOCUMENTS 3,670,630 A    6/1972 Tyson et al.
4,634,214 A    1/1987 Cannon, Jr. et al.
(Continued)

FOREIGN PATENT DOCUMENTS

EP        0992343 A1    4/2000
WO   WO2004097988 A2   11/2004
(Continued)

OTHER PUBLICATIONS

International Search Report of application PCT/US2017/025635, dated Aug. 24, 2017, 2 pages.

*Primary Examiner* — Rhonda S Peace
(74) *Attorney, Agent, or Firm* — Christensen, Fonder, Dardi & Herbert PLLC

(57) ABSTRACT

A delivery system extends from a laser radiation source for connecting to a medical device that utilizes the laser radiation for medical treatment. The delivery system comprises an optical fiber connecting to a male launch connecter. The male launch connector having a body portion with the optical fiber fixed or constrained therein and the optical fiber terminating at a male ferrule with a forward directed fiber facet, the male ferrule may be compliantly supported and positioned by elastomeric material positioned between the male ferrule and the body portion. The launch connector engages a receiving connector first with mechanical connection portions and then more finely aligning optical connection portions by the male ferrule self aligning in a female ferrule with cooperating tapered surfaces. The male portion may fully seat in the female portion with cooperating cylindrical surfaces.

20 Claims, 5 Drawing Sheets

Related U.S. Application Data continuation of application No. 15/476,961, filed on Mar. 31, 2017, now Pat. No. 10,082,632.

(60) Provisional application No. 62/428,269, filed on Nov. 30, 2016, provisional application No. 62/317,296, filed on Apr. 1, 2016.

(51) Int. Cl.
*G02B 6/36* (2006.01)
*A61N 5/06* (2006.01)
*A61B 18/22* (2006.01)
*A61N 5/067* (2006.01)

(52) U.S. Cl.
CPC ......... *G02B 6/3861* (2013.01); *G02B 6/3887* (2013.01); *G02B 6/3893* (2013.01); *G02B 6/3897* (2013.01); *G02B 6/4206* (2013.01); *G02B 6/4292* (2013.01); *G02B 6/4295* (2013.01); *A61B 18/22* (2013.01); *A61N 5/067* (2021.08); *A61N 2005/063* (2013.01); *A61N 2005/0632* (2013.01)

(56) References Cited

U.S. PATENT DOCUMENTS

| | | | |
|---|---|---|---|
| 4,747,656 A | 5/1988 | Miyahara et al. | |
| 4,991,929 A | 2/1991 | Bowen et al. | |
| 5,121,454 A | 6/1992 | Iwano et al. | |
| 5,329,541 A | 7/1994 | Brown | |
| 5,337,386 A | 8/1994 | Noll et al. | |
| 5,574,815 A | 11/1996 | Kneeland | |
| 5,640,478 A | 6/1997 | Roller | |
| 5,907,650 A | 5/1999 | Sherman et al. | |
| 5,943,460 A | 8/1999 | Mead et al. | |
| 6,065,882 A | 5/2000 | Roller et al. | |
| 6,238,103 B1 | 5/2001 | Ezawa | |
| 6,282,349 B1 | 8/2001 | Griffin | |
| 6,394,665 B1 | 5/2002 | Hayashi | |
| 6,432,047 B1 * | 8/2002 | Gust | A61B 1/042 385/117 |
| 6,618,405 B2 | 9/2003 | Kimura et al. | |
| 6,626,582 B2 | 9/2003 | Farrar et al. | |
| 6,953,288 B2 * | 10/2005 | Foley | G02B 6/4292 385/60 |
| 7,290,915 B2 * | 11/2007 | Solovay | G02B 6/4298 362/572 |
| 7,503,701 B2 | 3/2009 | Hiereth et al. | |
| 7,857,523 B2 | 12/2010 | Masuzaki | |
| 8,064,742 B2 * | 11/2011 | Watanabe | G02B 6/262 385/31 |
| 8,419,293 B2 | 4/2013 | Zerfas et al. | |
| 8,714,836 B2 | 5/2014 | Daikuhara | |
| 8,888,378 B2 | 11/2014 | Zerfas et al. | |
| 9,057,847 B2 | 6/2015 | Lin | |
| 9,160,130 B2 * | 10/2015 | Daikuhara | G02B 6/4206 |
| 9,329,350 B2 | 5/2016 | Zerfas et al. | |
| 9,393,081 B2 | 7/2016 | Hiereth et al. | |
| 9,395,496 B2 | 7/2016 | Byer et al. | |
| 9,429,713 B2 | 8/2016 | Thornton, Jr. | |
| 9,465,173 B2 | 10/2016 | Becker | |
| 9,804,339 B2 * | 10/2017 | Fukuoka | G02B 1/115 |
| 9,933,583 B2 | 4/2018 | Yan et al. | |
| 2002/0081080 A1 * | 6/2002 | Balle-Petersen | G02B 6/4296 385/93 |
| 2002/0159714 A1 | 10/2002 | Lampert | |
| 2004/0213524 A1 * | 10/2004 | Foley | G02B 6/4292 385/88 |
| 2005/0067237 A1 | 3/2005 | Schurmans | |
| 2013/0084042 A1 | 4/2013 | Bouchard et al. | |
| 2015/0374207 A1 | 12/2015 | Fukouka | |
| 2017/0285276 A1 | 10/2017 | Altshuler et al. | |

FOREIGN PATENT DOCUMENTS

| | | |
|---|---|---|
| WO | WO2005119319 A2 | 12/2005 |
| WO | WO2010124165 A1 | 10/2010 |
| WO | WO2013126429 A2 | 8/2013 |
| WO | WO2014151927 A1 | 9/2014 |

\* cited by examiner

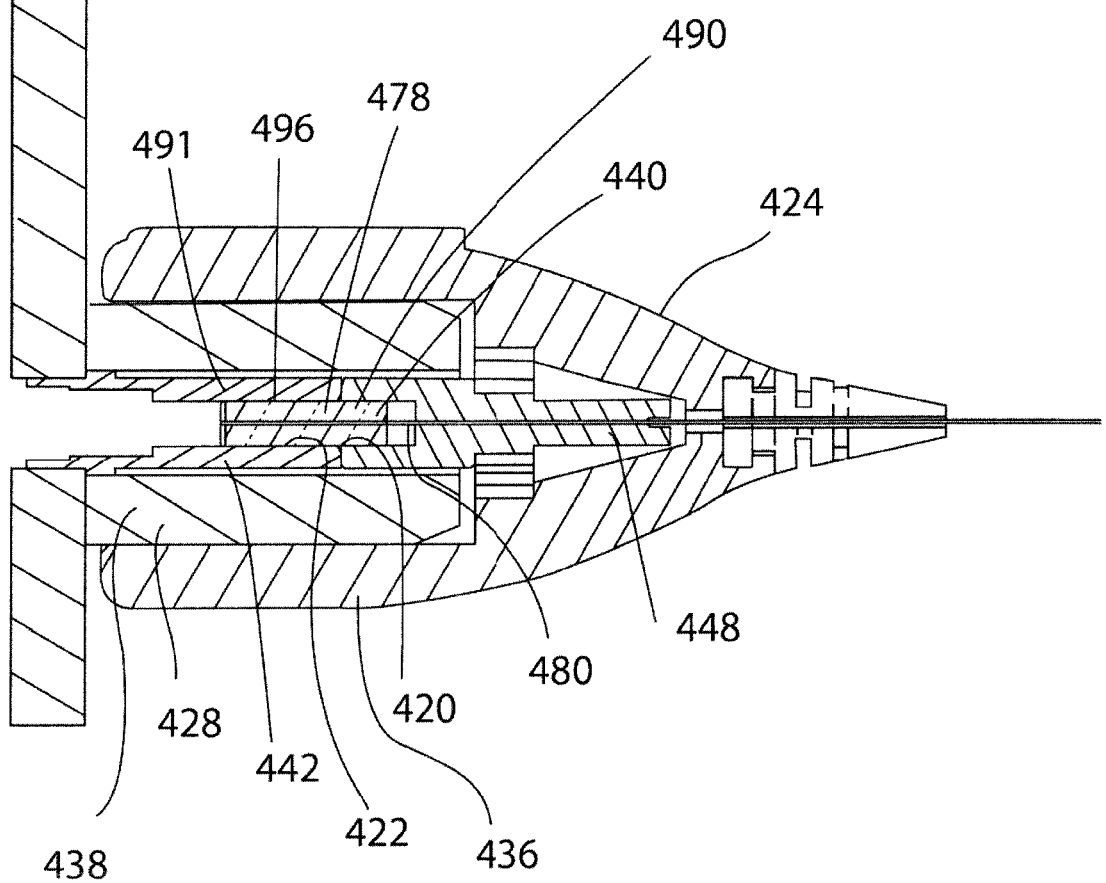

OPTICAL FIBER CABLE CONNECTOR

CROSS-REFERENCE TO RELATED APPLICATIONS

This application is a continuation of U.S. patent application Ser. No. 16/141,381, filed Sep. 25, 2018, now U.S. Pat. No. 10,663,677 which is a continuation of U.S. patent application Ser. No. 15/476,961, filed Mar. 31, 2017, now U.S. Pat. No. 10,082,632, which claims the benefit of U.S. Provisional Application No. 62/428,269, filed Nov. 30, 2016 and U.S. Provisional Application No. 62/317,296, filed Apr. 1, 2016, the disclosures of which are incorporated by reference herein in their entireties.

BACKGROUND OF THE INVENTION

Laser-based medical devices use laser radiation for medical treatments. The laser radiation type, power, and parameters vary depending upon the treatment. A laser source connects to a medical device using a delivery system having an optical fiber and an optical connector that couples to an interface of a medical device. The delivery system could be single use or reusable depending on the medical treatment and regulations.

The optical connector is a critical component the delivery system. Generally the size of optical fiber connectors have decreased over time due to the desirability of a higher density of connectors on telecommunications equipment; that is, more connectors per square inch of equipment space. Typical connectors for medical purposes comprise slightly modified optical connectors developed for telecommunication devices use, such as SMA-905 or SMA-906 modified connectors with a forward projecting ferrule with an exposed fiber facet. Such connectors are of small size and the mating components are also small, specifically, the ferrule securing the optical fiber and the cooperating female component. The small size of the graspable portion requires delicate manipulations to make the optical fiber connection to the medical device. The small sized connectors are not conducive to handling with gloves, nor making a quick connection. Also, it is easy to contaminate or damage the input fiber facet during mating with medical device as the facet is exposed and defines the furthermost portion of the connector. Any issue associated with the integrity of the connection between the laser source and medical device can impact the performance of the medical device and potentially the medical procedure.

Thus, improvements in connector design (both parts, at laser device output and at the input of delivery system) that are ergonomically advanced (including handling with gloves), safer, easier to mate, more robust, and less prone to damage or contamination of the fiber facet, more economical to manufacture and use, would be well received by the medical industry. Moreover, a means for confirming the integrity of the connection would be advantageous. Additionally, improvements in affordability would be well received.

SUMMARY

A delivery system extending from a laser radiation source for connecting to a medical device that utilizes the laser radiation for medical treatment. The delivery system comprises an optical cable with an optical fiber extending from the laser source with a male launch connecter having a male ferrule on the optical cable. The launch connector couples to a receiving connector having a female ferrule that interfaces with the male ferrule on the medical device. The male launch connector having a body portion with an outer tubular portion projecting forward with an outermost or forwardmost edge and having a central axial recess defined therein. The optical fiber terminating at the male ferrule positioned in the central recess rearward of the forwardmost edge and presenting a forward facing fiber facet. In embodiments, the optical fiber fixed with respect to the body portion of the connector at an anchor point on the optical fiber rearwardly of the ferrule such that a dangling or cantilevered portion of the optical cable or fiber supports the ferrule. In embodiments the optical cable or fiber is the exclusive support of the male ferrule before the launch connector is connected to the receiving connector. The ferrule having freedom of movement provided by the flexibility of the optical cable forward of the anchor position. The ferrule may be constrained laterally by structure within or part of the body portion such as a tubular portion of the body portion thereby limiting the lateral freedom of movement. Such structure providing a circumferential gap around the ferrule for the entire length of the ferrule when the ferrule is axially centered within the tubular portion. In embodiments a resilient material may be attached to the rearward end portion of the male ferrule for controlling the radial or lateral freedom of movement that does provide some resistance to lateral movement beyond that provided by the optical fiber or cable.

In embodiments, the ferrule having registration surfaces such as an outer cylindrical surface that registers with a cooperating inwardly facing cylindrical surface on the female ferrule of the receiving connector without the female ferrule having an axial stop for the male ferrule in the optical registration receiver. The inventors have recognized that the criticality of the axial placement, that is, the forward rearwardly axial position of the male ferrule with respect to the female ferrule is substantially less that the criticality of the centration alignment, that is, the radial and axial alignment of the ferrule. Conventional optical fiber connector art rely upon axial stop surfaces that are part of the ferrule or rigidly and directly connected to the ferrule. Embodiments herein provide suspension of the ferrule in the male connector only by the optical cable or fiber rearward of the ferrule and a seating interface with the optical registration component, such as a female ferrule, in a cylindrical interface with no axial stop surfaces on the ferrule or directly fixed with respect to the ferrule. The forward-backward axial position of the ferrule is controlled by the optical cable or fiber extending rearward from the ferrule that is attached directly or indirectly to the connector body. Such an arrangement provides an economical, simple, and reliable connection configuration with the needed centration, that is, precise radial and axial alignment, and sufficient axial forward-rearward positional placement.

In embodiments of the invention, the optical fiber rearwardly of the ferrule is fixed to an elastomeric support member providing axial cushioning and or resilience when the ferrule engages with a portion of the connector of the medical device. In embodiments, the forward face of the male ferrule, for example a chamfer surface has a tapered to cooperate with a like shaped concave recess in the female ferrule of the receiving connector of the medical device. The fixation of the optical fiber with respect to the launch connector body may be in resilient elastomeric disks defining diaphragms.

In embodiments of the invention, the ferrule is slidingly received in a bore of an optical registration receiver, the optical registration receiver may have a tapered concave lead-in registration surface and a cylindrical registration surface, the male ferrule having a cooperating convex outer tapered surface and a cylindrical registration surface to closely engage the cylindrical registration surface of the optical registration receiver.

In embodiments of the invention, the outer tubular portion of the launch connector engages with a mechanical registration receiver of the receiving coupling attached to, for example, the medical device. r, the leading edge of the tubular outer portion and/or the outermost edge of the mechanical registration receiver may be tapered to provide an insertion tolerance.

A feature and advantage of embodiments of the invention is an optical fiber connector with graspable body portion and having a single fiber that has an internal floating ferrule and a graspable handle of an enlarged sized, in embodiments the diameter of a central lengthwise portion of the graspable portion is from 5 to 20 mm. In embodiments the diameter of a central lengthwise portion of the graspable portion is from 8 to 16 mm.

A feature and advantage of embodiments of the invention is an optical fiber launch connector with a single fiber that has an internal movable ferrule fixed only to the single optical fiber and optionally to sheaths on the fiber. The ferrule positionally constrained by but not positionally fixed by being partially positioned in the bore of an inner tubular portion of the launch connector.

A feature and advantage of embodiments of the invention is a optical fiber coupling with cooperating connectors, one connector being a launch connector with a ferrule supporting an optical fiber with a fiber facet, the other connector receiving the one connector and having an optical registration receiver that receives the ferrule. Each connector having the optical connecting portion of the connector recessed from the exterior of the connector.

In embodiments, a cooperating pair of optical fiber connectors for connecting a laser source to a medical device for delivery of laser energy, each connector having an outer mechanical coupling portion and an inner optical coupling portion, each of the outer mechanical coupling portions configured as an outer tubular portion with a forward edge, each outer tubular portion having a tubular wall and defining respective axial recesses, the optical coupling portions concentrically positioned within the axial recesses and spaced from the tubular walls, the optical coupling portions inset from the respective forward edges. In embodiments, one connector provides an optical cable with a optical fiber connecting to a ferrule and presenting a fiber facet. The ferrule having a central position, the ferrule received within a female portion of an optical registration receiver. In embodiments, one of the tubular mechanical coupling portions interlaced between the tubular mechanical coupling portion of the other coupling and the optical coupling portion of the other coupling. The tubular mechanical coupling portions slidingly engaged with one another. In embodiments the connector supplying the laser energy to the medical device, a launch connector, has its outer tubular portion extending within the outer tubular portion of the connector associated with the medical device. In embodiments, as the connectors are manually manipulated, the outer mechanical couplings engage first and bring the connectors into an axial alignment as the outer mechanical couplings are slidingly engaged and brought together, the connectors become axially aligned before the optical coupling portions engage each other. The optical coupling portions then are prealigned and as the optical coupling portions engage with tapered surfaces on one or both optical coupling portion, the optical couplings are brought into final operational alignment. In embodiments one optical coupling portion is laterally movable with respect to its respective mechanical coupling portion.

DESCRIPTION OF THE FIGURES

FIG. 7 illustrates an embodiment with the outer mechanical connection portion of the launch connector exterior to the mechanical connection portion of the medical device mechanical connection portion.

DETAILED DESCRIPTION

Figure 1:
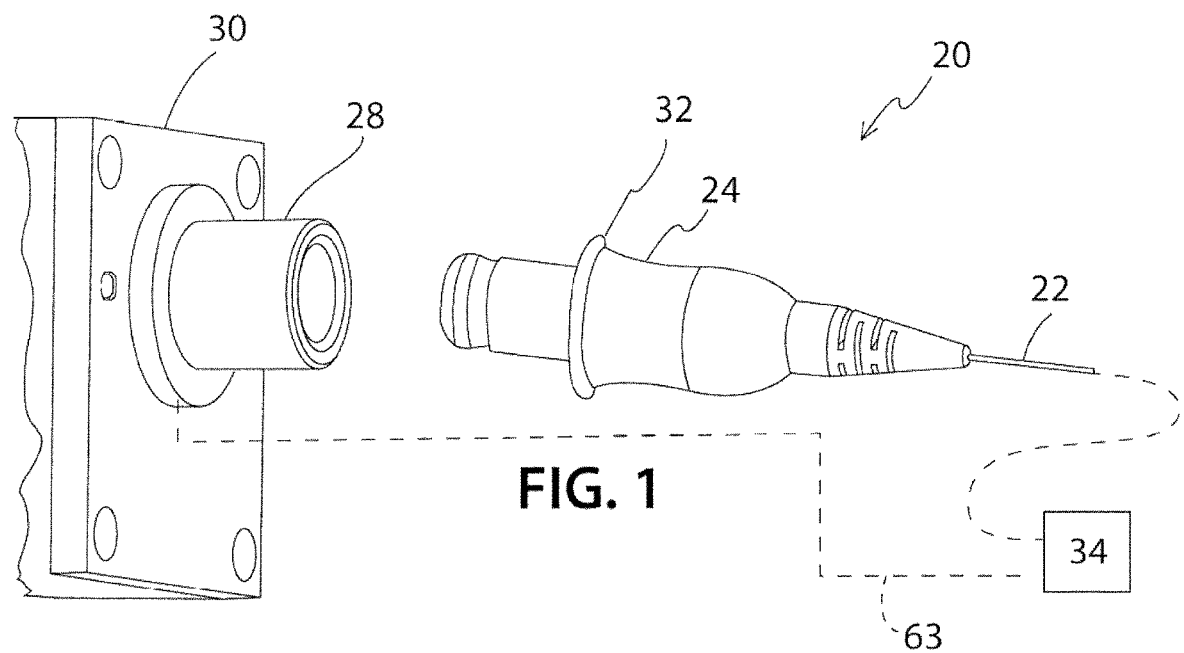
FIG. 1 is a perspective view of a delivery system with a launch connector disconnected from a connector on a medical device in accord with inventions herein.
Figure 2:
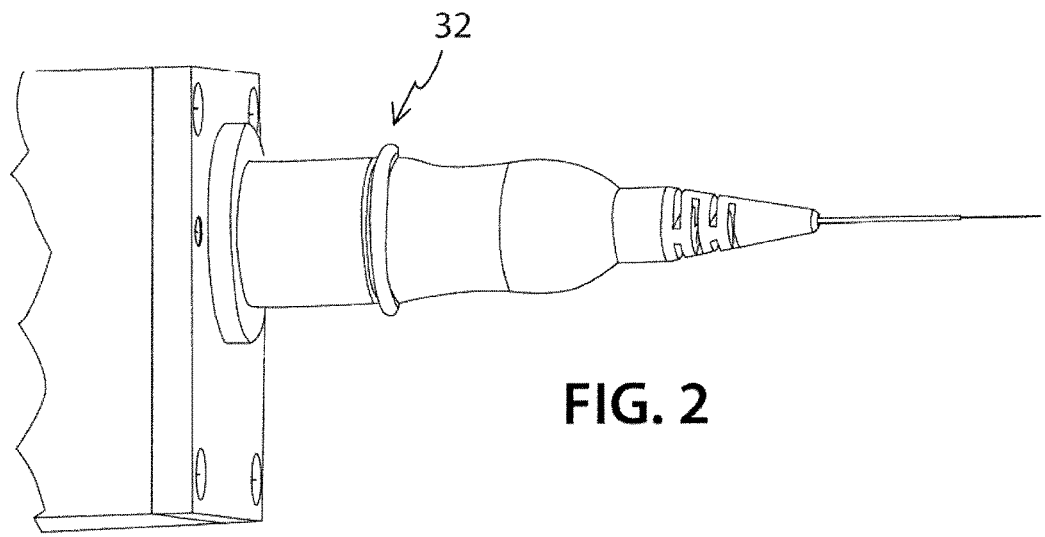
FIG. 2 is a perspective view of a coupling for a laser radiation delivery system connected to a medical device in accord with embodiments of the invention.

Referring to FIGS. 1 and 2, a delivery system 20 comprises a optical fiber cable 22 and a launch connector 24. The launch connector 24 and a connector 28 on a medical device 30 defining an optical fiber coupling 32 for providing laser radiation to the medical device 30 from the laser radiation source 34.

Figure 3:
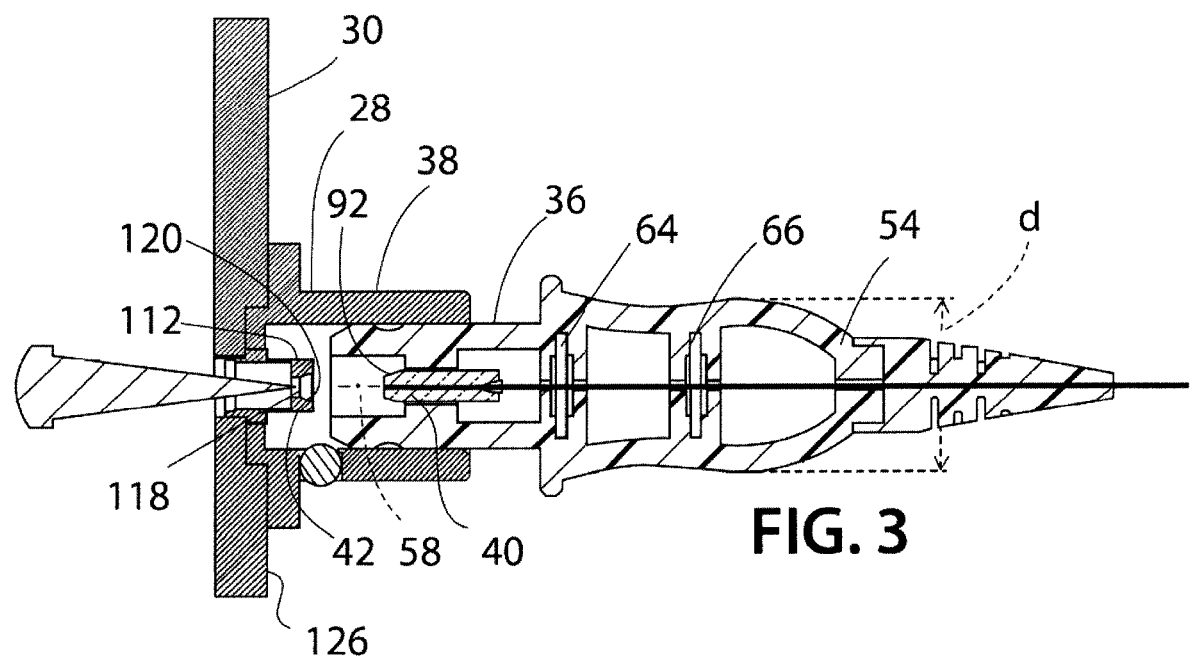
FIG. 3 is a cross sectional view of the coupling of FIG. 2 in a partial mechanical coupling in accord with embodiments of the invention.
Figure 4:
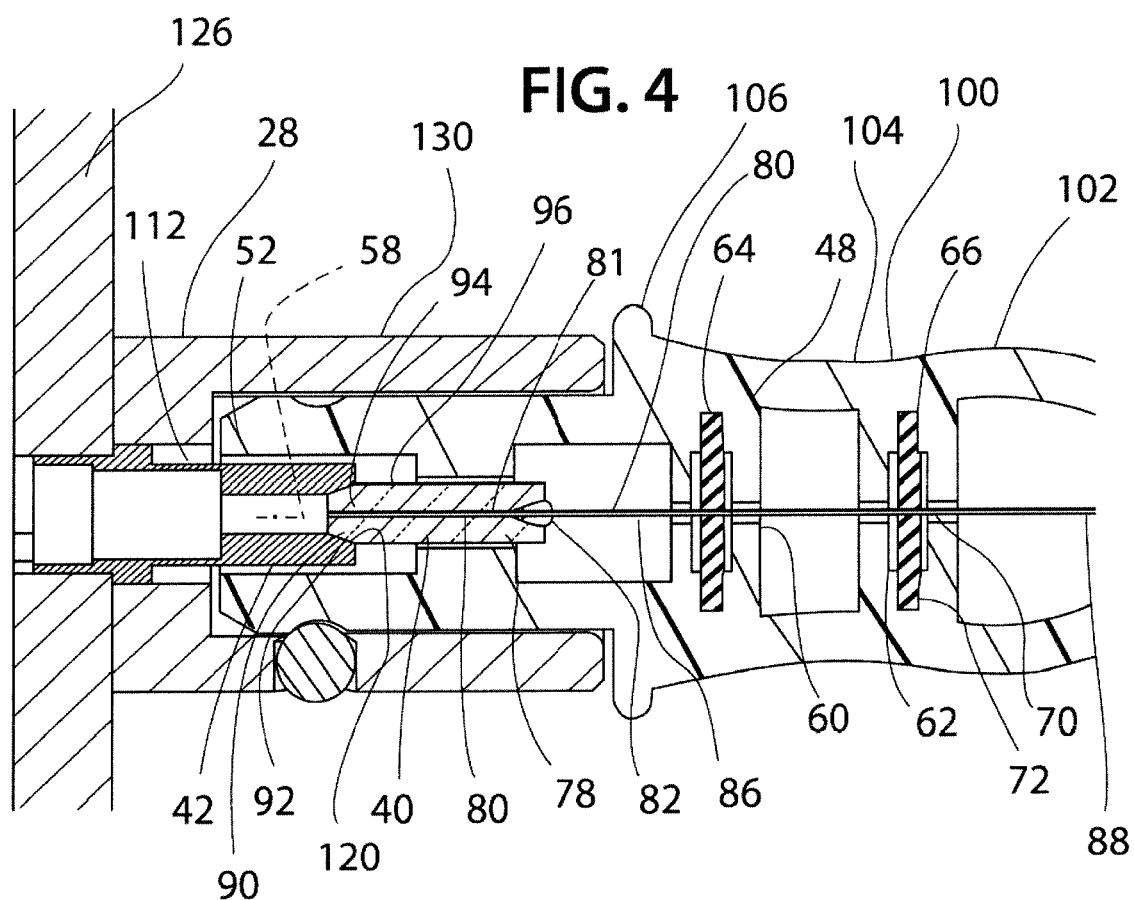
FIG. 4 is a detailed cross sectional view of FIG. 3 showing the mechanical coupling and optical coupling with a frustoconical registration of the ferrule and optical registration receiver optical coupling in accord with embodiments of the invention.

Referring to FIGS. 1-4, each of the connectors 24, 28 have a mechanical connection portion 36, 38 and respective optical connection portion 40, 42 configures as a male ferrule and a female ferrule respectively. The launch connector 24 has a body portion 48 that extends from a forward or proximal end 52 to a rearward or distal end 54 of the connector 24. A strain relief tail portion 56 provides transitional support to the optical fiber cable as it exits the connector. The optical fiber cable extends axially along a central axis 58 in apertures 60 of the body portion such that the cable may be spaced from inward surfaces 62 of the body portion. In the embodiment of FIGS. 3 and 4, the optical fiber cable is supported by a compliant fiber supports 64, 66. The compliant fiber supports may be disc shaped with the fiber fixed to the center 70 of the discs 64, 66, such as by adhesive and with the disc supported at its peripheral portion 72 by the body portion 48. The compliant fiber supports 64, 66 may provide axial displacement capability and cushioning of the optical connection portion 40 with respect to the body portion of the launch connector 24.

The mechanical connection portion of the launch connector is a mechanical registration guide configured as a tubular end portion 36.

The optical connection portion 40 of the launch connector 24 comprises a ferrule 78 with an optical fiber 80 fixed in a axial bore 81 therein such as by adhesive 82. The optical fiber may have two or more sheathings 86, 88 covering the fiber rearward of the ferrule 78. The ferrule 78 may have a frustoconical portion 90 with a tapered surface 92 at its forward end 94 and rearward of the tapered surface have a cylindrical surface 96. The ferrule may be formed of conventional materials such as glass, bronze, other metals, and ceramic materials.

The launch connector 24 has a graspable portion 100 for manual manipulation of the connector. The graspable portion may have a bulbous portion 102, a recessed portion 104, and a forward lip 106, all facilitating handling of the connector, particularly in a medical setting where users may be wearing gloves and ready and quick access and control of the connector is advantageous. The diameter d of the graspable portion may be from 5 to 20 mm in embodiments. In other embodiments the diameter of the graspable portion may be from 8 to 16 mm. The graspable portion 100 may be unitary or integral with the body portion 48 of the launch connector 24 and may be formed of polymers including, for example, thermoplastic elastomers.

The medical device connector 28 has the optical coupling portion 42 which couples with the optical connection portion 40 of the launch connector. The optical connection portion comprises an optical registration receiver configured as a female ferrule 112 formed of ceramic material, glass, metal, or other conventional materials. A recess 118 is defined by a reverse frustoconical surface 120 that conforms to the tapered surface 92 of the launch connector optical coupling portion configured as a male ferrule 40. The female ferrule is fixed to a body portion 122 of the medical device connector and the medical device connector is attached to a wall 126 or other structure of the medical device. The body portion, or other structure of the connector 28 provides a mechanical registration receiver 130 configured as a tubular portion 38 that conforms to and snugly receives the tubular portion 36 of the launch connector.

Referring to FIGS. 3 and 4, the coupling is made by the tubular portion 36 of the launch connector 24 initially being partially inserted into the mechanical connection portion 38 of the medical device connector 28, as shown in FIG. 3. The connectors are in an axial alignment, this provides a gross or prealignment of the optical connection portions before they make contact or are engaged, that is, the connectors can only move axially and rotationally with respect to one another. As shown in FIG. 4, when the optical coupling portions make contact the ferrule and optical registration receiver self-align by way of the conforming cooperating surfaces 92, 120 and the ferrule 78 and optical fiber 80 are slightly displaced rearwardly facilitated by the compliant members 64, 66. When the launch connector is fully seated the optical connection portions are fully engaged.

Figure 5A:
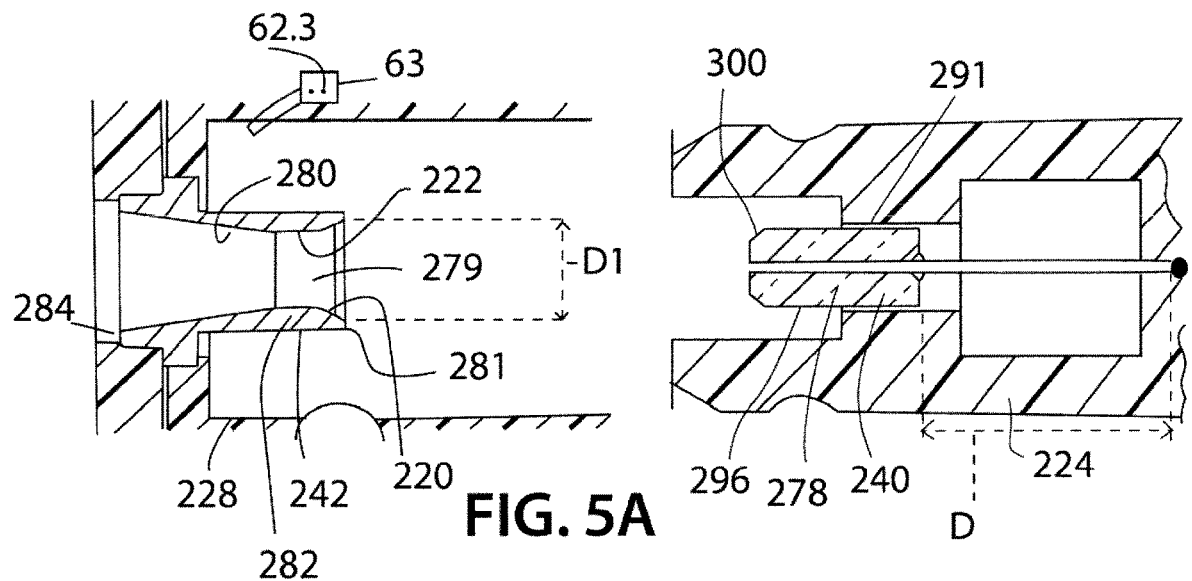
FIG. 5A is a cross sectional view of an embodiment of a coupling illustrating mechanical connection portions and optical connection in a pre-connection condition.
Figure 5B:
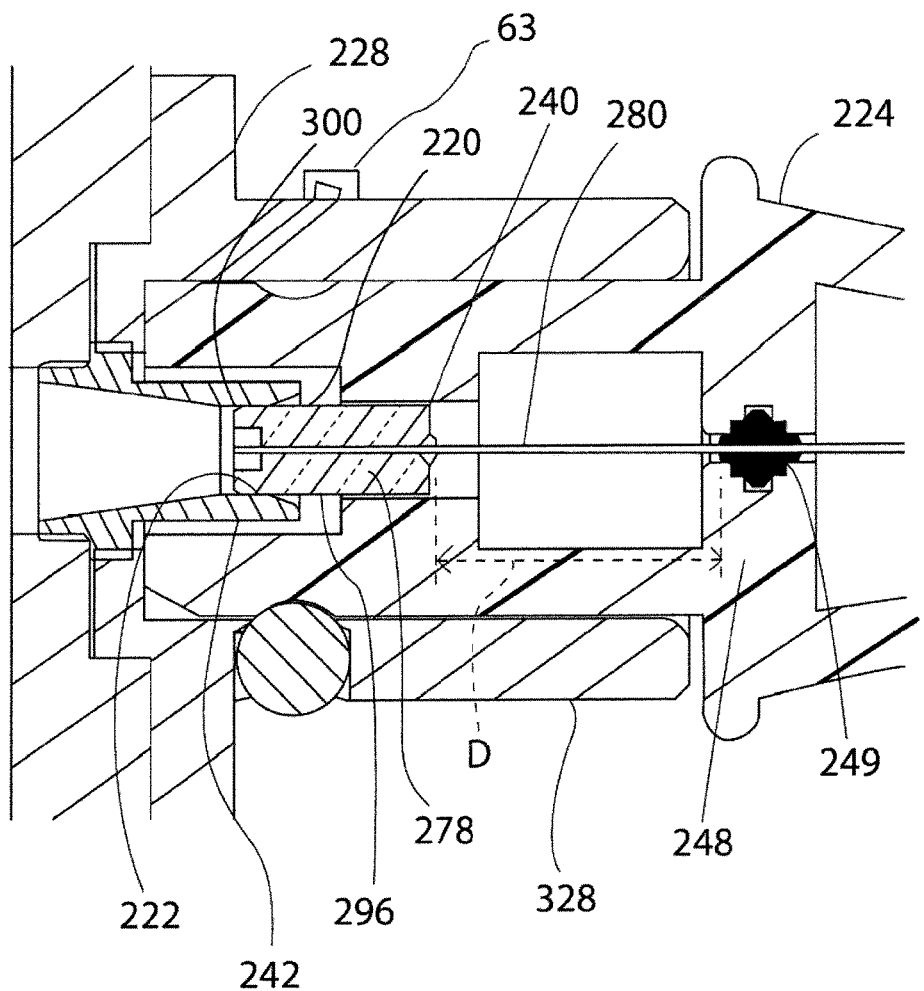
FIG. 5B is a cross sectional view of the coupling of FIG. 5A with a cylindrical registration of a male ferrule and the female ferrule in accord with embodiments of the invention.

Referring to FIGS. 5A and 5B, another embodiment is illustrated with launch connector 224 and a medical device connector 228. The medical device optical coupling portion, configured as a female ferrule 242, has a tapered lead-in surface 220 and a cylindrical seating surface 222. The optical coupling portion 240 of the launch connector 224 comprises a ferrule 278 with a cylindrical outer surface 296 and chamfered guide-in surface 300. The optical coupling portion further comprising an optical fiber line 280 that is fixed to the body portion 248 such as by adhesive 249. The optical fiber line 280 and ferrule may cantilever outwardly from the body portion providing lateral movement capability of the ferrule such that the optical connection portions may self-align when they initially engage. The optical fiber line includes an optical fiber and may include sheathing or other layers on the optical fiber. When the ferrule 278 is finally seated in the female ferrule, the coupling is complete, there is no axially loading on the optical connection portion of the launch connector 224. There are no stop surfaces on the female ferrule to axially position, forward-rearwardly, the male ferrule. The female ferrule may have a throughhole 279 that and internal surface 280 with a diameter D1 that converges from a first side 281 to a mid portion 282 with a cylindrical surface 222, and then diverges to the second side 284 resulting in an hour glass shape. The male ferrule 278 is separated from an anchored position 288 by a distance D. In embodiments this distance is 4-15 mm, or thereabout. In embodiment distance D is 6 to 11 mm. The male ferrule cantilevers forwardly by the optical fiber line and has a gap 292, that is, space, between the outer surface of the male ferrule and the body portion of the connector.

Similar to the embodiment of FIGS. 3 and 4, the tubular portions of the mechanical connection portion of the embodiments of FIGS. 5A and 5B first engage to provide a gross alignment of the optical connection portions, then the optical portions engage, self align by movement of the male ferrule, and then fully engage with cylindrical surface seating on cylindrical surface. The forward-rearward placement is not as critical to coupling performance as the radial and axial alignment.

Means 63, schematically shown, for confirming complete coupling is provided on the medical device and connecting to the laser source to prevent the laser for operating if the coupling is not fully coupled. Such can be by way of micro switches, 63.2, and other means known in the art. Such means may provide a lock-out of the laser radiation source. That is, unless the complete connection of the coupling is verified, the laser light source is not allowed to generate the laser radiation.

Figure 6:
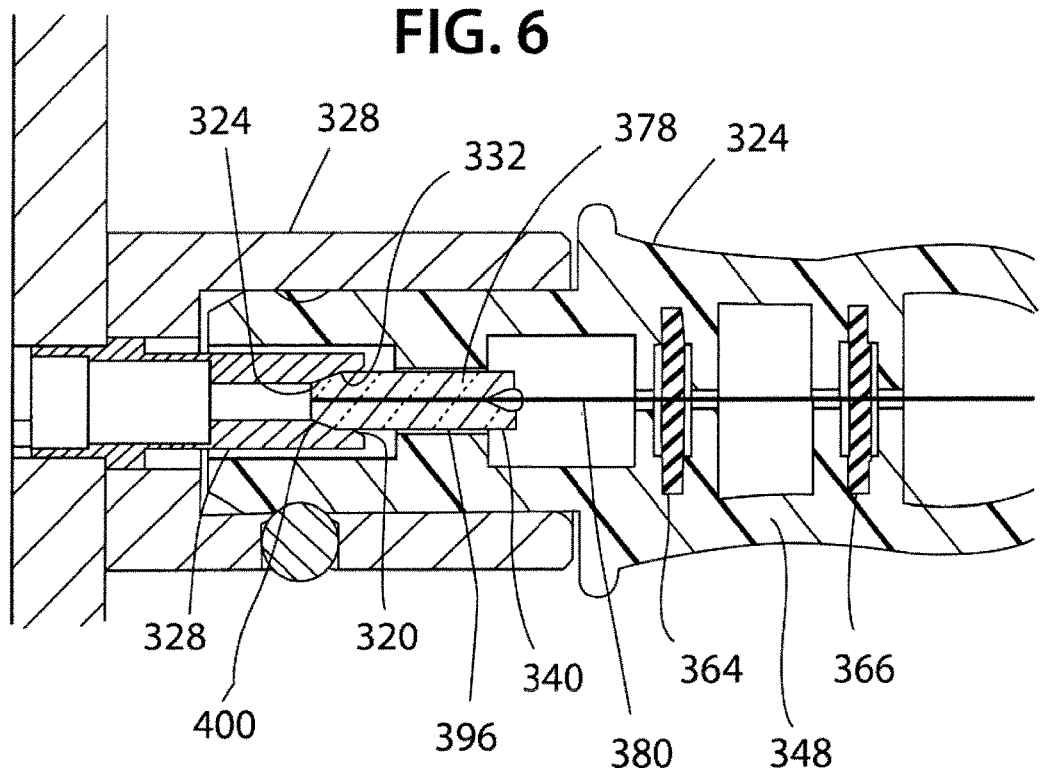
FIG. 6 is a cross sectional view of a coupling with cylindrical registration and a conical registration of a male ferrule and with a stop surface in the optical registration receiver.

Referring to FIG. 6, another embodiment is illustrated with launch connector 324 and a medical device connector 328. The medical device optical coupling portion 342 has a tapered lead-in surface 320 and a cylindrical seating surface 322 and a stop surface 324. The optical coupling portion 340 of the launch connector 324 comprises a ferrule 378 with a cylindrical outer surface 396 and a tapered forward surface 400. The optical coupling portion further comprising an optical fiber 380 that is compliantly attached to the body portion 348 through compliant members 364, 366. The optical fiber 380 and ferrule may cantilever outwardly from the body portion providing lateral movement capability of the ferrule such that the optical connection portions may self-align when they initially engage. Upon final seating of the ferrule in the optical registration receiver the ferrule and optical fiber may be slightly displaced rearward facilitated by the compliant members.

Referring to FIG. 7, another embodiment is illustrated with launch connector 424 and a medical device connector 428. The medical device optical coupling portion 442 has a tapered lead-in surface 420 and a cylindrical seating surface 422. The optical coupling portion 440 of the launch connector 424 comprises a ferrule 478 with a cylindrical outer surface 496. The optical coupling portion further comprising an optical fiber 480 that is fixed to the body portion 448. The optical fiber 480 and ferrule may cantilever outwardly from the body portion providing lateral movement capability of the ferrule such that the optical connection portions may self-align when they initially engage. The bore 490 of the body portion constrains laterally the ferrule allowing some lateral movement of the ferrule. Upon final seating of the ferrule in the optical registration receiver 491 the ferrule and optical fiber are not under axial loading. The mechanical connection portion 436 of the launch connector envelops the mechanical connection portion 438 of the medical device mechanical connection portion which is different than the embodiments illustrated in FIGS. 1-6.

Figure 8:
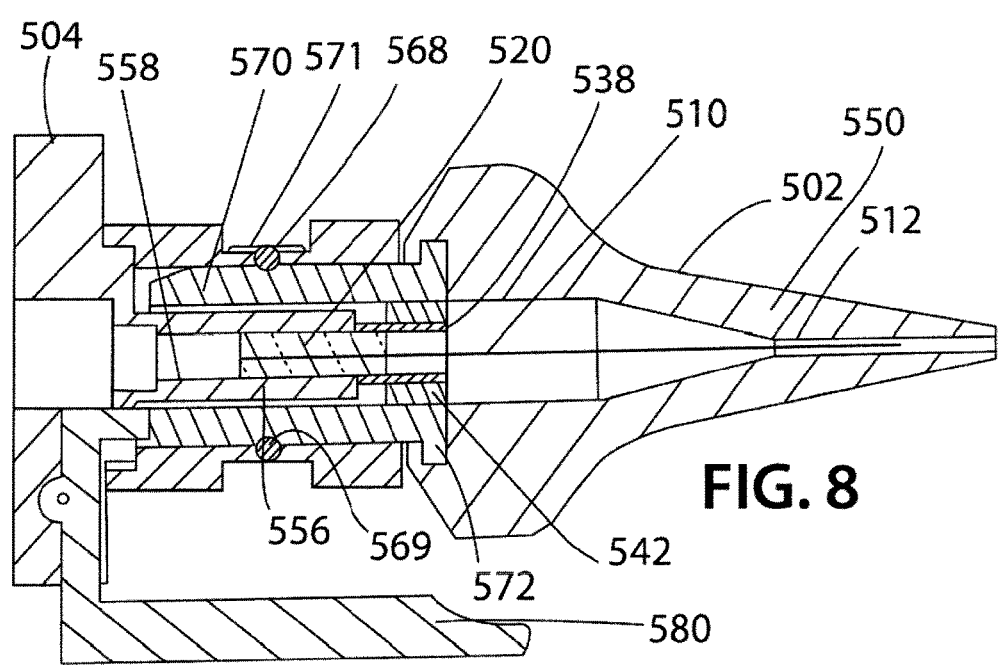
FIG. 8 is a cross sectional view of coupling according to embodiments.

Referring to FIG. 8, another embodiment is illustrated with a launch connector 502 and a receiving connector 504. In this embodiment the optical fiber line 510 has a optical fiber with multiple layers of sheathing 512 removed in the connector. The male ferrule is a high precision glass male ferrule 520 connecting to sleeve 538 that connects to compliant material, such as a thermoplastic elastomer, configured as a ring 542, provides slight compliance along all axis. The launch connector has a strain relief boot 550 for the optical fiber line 510. The female ferrule 556 has a precision bore 558 that engages and aligns the male ferrule 520 in centration and axial position. A ball detent mechanism 568 including a circumferential spring 571 engages with a exterior groove 569 in the tubular portion 570 of the body portion 572 of the launch connector. A latch arm 580 pivots about the body portion of the receiving connector 504 to push out the launch connector.

The mechanical connection portions may be configured as bayonet connections, screw on connections, press fit connections, or detent connections.

The following U.S. patents are incorporated by reference for all purposes: U.S. Pat. Nos. 5,329,541; 5,907,650; 5,943,460; 6,238,103; 7,503,701; 8,419,293; 8,888,378; 9,329,350; 9,393,081; 9,395,496; and 9,429,713.

The invention is not restricted to the details of the foregoing embodiment (s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

We claim:

1. An optical fiber connector coupling for connecting a laser radiation source to a device, the coupling comprising a launch connector with a mechanical connection portion comprising a body portion and an optical connection portion comprising a male ferrule connected to an optical fiber, the male ferrule connecting to and supported by the body portion exclusively through a) the optical fiber extending rearwardly from the male ferrule and anchored with respect to the body portion and b) a compliant elastomeric material positioned intermediate the male ferrule and the body portion, wherein the male ferrule is compliantly and resiliently positioned and supported within the body portion of the launch connector axially and radially such that the ferrule is movable with respect to the body portion with resistance to such movement, the male ferrule having a cylindrical outer surface, the coupling further comprising a receiving connector, the receiving connector comprising a mechanical connection portion for cooperating with the mechanical connection portion of the launch connector, and an optical connection portion comprising an optical registration receiver, the optical registration receiver of the receiving connector not having an optical fiber associated therewith, the optical registration receiver having an internal cylindrical surface that slidingly engages the cylindrical outer surface of the male ferrule.

2. The optical fiber connector coupling for connecting a laser radiation source to a device of claim 1, wherein the optical fiber line extending from the male ferrule is anchored with respect to the body portion at an anchor position that is rearward of the elastomeric material.

3. The optical fiber connector coupling of claim 1, further comprising a sleeve extending about the male ferrule, the male ferrule extending forwardly from the sleeve, the elastomeric material extending between the sleeve and the body portion.

4. The optical fiber connector coupling of claim 3, wherein the compliant elastomeric material has a ring shape and directly engages the body portion.

5. The optical fiber connector coupling of claim 3, wherein a forward face of the sleeve provides a stop surface with the optical registration receiver.

6. An optical fiber connector coupling for connecting a laser radiation source to a device, the coupling comprising a launch connector with a mechanical connection portion and an optical connection portion, the optical connection portion having a cylindrical outer surface, the coupling further comprising a receiving connector, the receiving connector comprising a mechanical connection portion for cooperating with the mechanical connection portion of the launch connector, and an optical connection portion comprising an optical registration receiver, the optical registration receiver having an internal cylindrical surface that slidingly engages the cylindrical outer surface of the optical connection portion, the optical registration receiver not having an internal stop surface limiting the insertion distance of the cylindrical outer surface into the optical registration receiver, the optical connection portion compliantly and resiliently supported within the body portion and with respect to the body portion of the launch connector by a resilient compliant member positioned intermediate the optical connection portion and the body portion whereby the optical connection portion is moveable with respect to the body portion with resistance to such movement.

7. The optical fiber connector coupling for connecting a laser radiation source to a device of claim 6, wherein the receiving connector does not have an optical fiber connecting thereto other than an optical fiber associated with the launch connector.

8. The coupling for connecting a laser radiation source to a device of claim 6, wherein the receiving connector comprises a sensor for detecting when the coupling is fully engaged.

9. The coupling for connecting a laser radiation source to a medical device of claim 8, wherein the sensor comprises an electrical switch that is actuated with the presence of a tubular portion of the launch connector in a cooperating tubular portion of the receiving connector.

10. The optical fiber connector coupling of claim 6, wherein the resilient compliant member is formed of an elastomer and directly engages the body portion.

11. The optical fiber connector coupling of claim 6, wherein the resilient compliant member is formed of an elastomer and directly engages the optical connection portion.

12. The optical fiber connector of claim 6, wherein the resilient compliant member is sleeve shaped and extends around an optical fiber extending rearwardly from the optical connection portion.

13. The optical fiber connector of claim 12, wherein the optical connection portion comprises a male ferrule with a metal sleeve thereon.

14. An optical fiber connector coupling for connecting a laser radiation source to a device, the coupling comprising a launch connector with a mechanical connection portion and an optical connection portion, the optical connection portion connected to an optical fiber extending rearwardly therefrom, the optical connection portion having a forward face, a forward cylindrical portion, and a cylindrical portion rearward of the forward cylindrical portion, the cylindrical portion rearward of the forward cylindrical portion being diametrically larger than the forward cylindrical portion, a compliant elastomeric material engaging a rearward portion of the optical connection portion and extending to an inwardly facing wall surface of a body portion of the launch connector wherein the optical connection portion is compliantly positioned and supported within the body portion of the launch connector such that the optical connection portion is movable within the body portion with resistance to such movement.

15. The optical fiber connector coupling of claim 14, wherein the optical connection portion of the launch connector comprises a male ferrule seated in a sleeve and wherein the forward cylindrical portion is defined by the male ferrule and the cylindrical portion rearward of the forward cylindrical portion is defined by the sleeve.

16. The optical fiber connector coupling of claim 15, wherein the elastomeric material engages the sleeve allowing movement of the sleeve with respect to the body portion and thereby movement of the male ferrule seated in the sleeve.

17. The optical fiber connector coupling for connecting a laser radiation source to a device of claim 14, further comprising a receiving connector for receiving the launch connector, the receiving connector comprising a mechanical connection portion for cooperating with the mechanical connection portion of the launch connector, and an optical connection portion comprising a female ferrule, the female ferrule having an internal cylindrical surface adjoining an internal conical surface, the internal cylindrical surface slidingly engages a cylindrical outer surface of the forward cylindrical portion of the optical connection portion of the launch connector when the connection is made, the female ferrule not having an internal stop surface in the female ferrule limiting the insertion of the cylindrical outer surface of the forward cylindrical portion into the female ferrule.

18. The optical fiber connector of claim 17, wherein the receiving connector does not have a optic fiber connecting directly thereto.

19. The optical fiber connector coupling for connecting a laser radiation source to a device of claim 17, wherein the female ferrule has an annular forward face that engages a surface of the optical connection portion of the launch connector, said surface positioned between the forward cylindrical surface and the cylindrical surface rearward of the forward cylindrical surface when the launch connector is fully connected with the receiving connector.

20. The optical fiber connector coupling for connecting a laser radiation source to a device of claim 17, wherein the female ferrule has a conical diverging portion positioned in front of a forward face of the male ferrule.

\* \* \* \* \*